United States Patent [19]
Dunham

[11] Patent Number: 5,797,948
[45] Date of Patent: Aug. 25, 1998

[54] CENTERING BALLOON CATHETER

[75] Inventor: Susan L. Dunham, Pembroke Pines, Fla.

[73] Assignee: Cordis Corporation, Miami, Fla.

[21] Appl. No.: 770,610

[22] Filed: Dec. 19, 1996

Related U.S. Application Data

[63] Continuation-in-part of Ser. No. 725,364, Oct. 3, 1996.
[51] Int. Cl.⁶ .................................................. A61M 25/10
[52] U.S. Cl. .............................. 606/194; 604/101; 600/7
[58] Field of Search ................... 604/101, 96; 606/194, 606/192; 600/7, 8

[56] References Cited

U.S. PATENT DOCUMENTS

| | | | |
|---|---|---|---|
| 4,878,495 | 11/1989 | Gray et al. | 604/101 X |
| 4,990,139 | 2/1991 | Jang | 604/101 |
| 4,994,033 | 2/1991 | Shockey et al. | 604/101 |
| 5,040,548 | 8/1991 | Yock . | |
| 5,049,132 | 9/1991 | Shaffer et al. | 604/101 |
| 5,061,273 | 10/1991 | Yock . | |
| 5,069,226 | 12/1991 | Yamauchi et al. . | |
| 5,171,383 | 12/1992 | Sagaye et al. . | |
| 5,199,939 | 4/1993 | Dake et al. . | |
| 5,238,004 | 8/1993 | Sahatjian et al. . | |
| 5,302,168 | 4/1994 | Hess . | |
| 5,308,356 | 5/1994 | Blackshear, Jr. et al. . | |
| 5,350,395 | 9/1994 | Yock . | |
| 5,383,853 | 1/1995 | Jung et al. . | |
| 5,409,015 | 4/1995 | Palermo . | |
| 5,411,476 | 5/1995 | Abrams et al. . | |
| 5,451,233 | 9/1995 | Yock . | |
| 5,496,346 | 3/1996 | Horzewski et al. . | |
| 5,501,227 | 3/1996 | Yock . | |
| 5,503,613 | 4/1996 | Weinberger . | |
| 5,503,614 | 4/1996 | Liprie . | |
| 5,540,659 | 7/1996 | Tierstein . | |
| 5,545,132 | 8/1996 | Fagan et al. . | |

FOREIGN PATENT DOCUMENTS

| | | |
|---|---|---|
| 93203354.1 | 11/1990 | European Pat. Off. . |
| WO 94/25106 | 11/1994 | WIPO . |

Primary Examiner—Michael H. Thaler

[57] ABSTRACT

In accordance with the present invention, there is provided a catheter for insertion into a vessel of a patient. The catheter has distal and proximal ends and is made from an elongated flexible shaft also having distal and proximal ends. The shaft has a central lumen extending therethrough which is substantially centered within the shaft. The shaft also having distal and proximal ends and further includes an inflation lumen. The catheter includes an inflatable, preferably non-compliant, outer balloon disposed at its distal end and an inflatable, preferably compliant, inner balloon disposed within the outer balloon. The inner balloon is in fluid communication with the inflation lumen for inflation and deflation thereof. The central lumen extends through the inner balloon. The inner balloon is a centering balloon, whereby when it is at least partially inflated the distal end of said central lumen is substantially centered within the vessel.

19 Claims, 8 Drawing Sheets

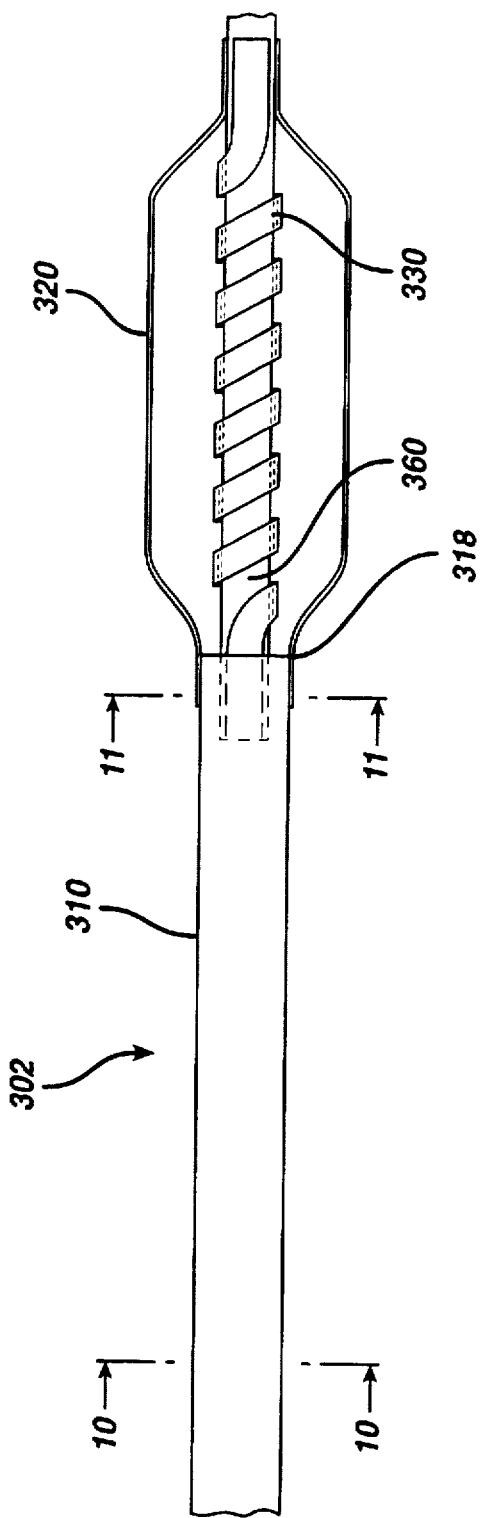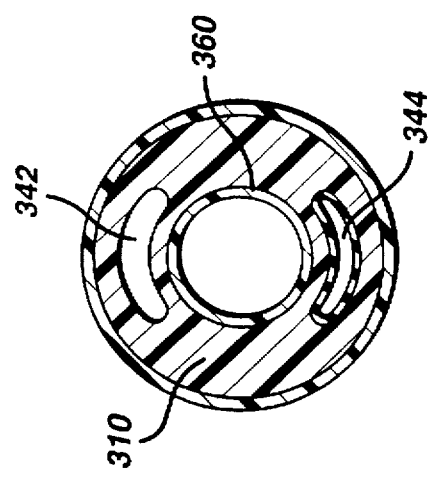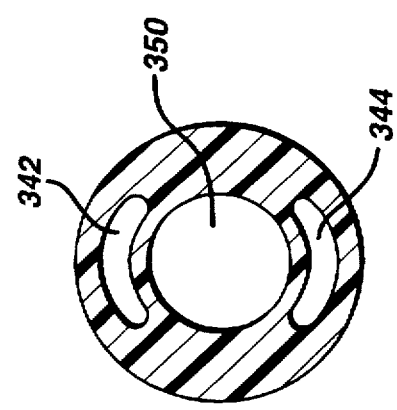

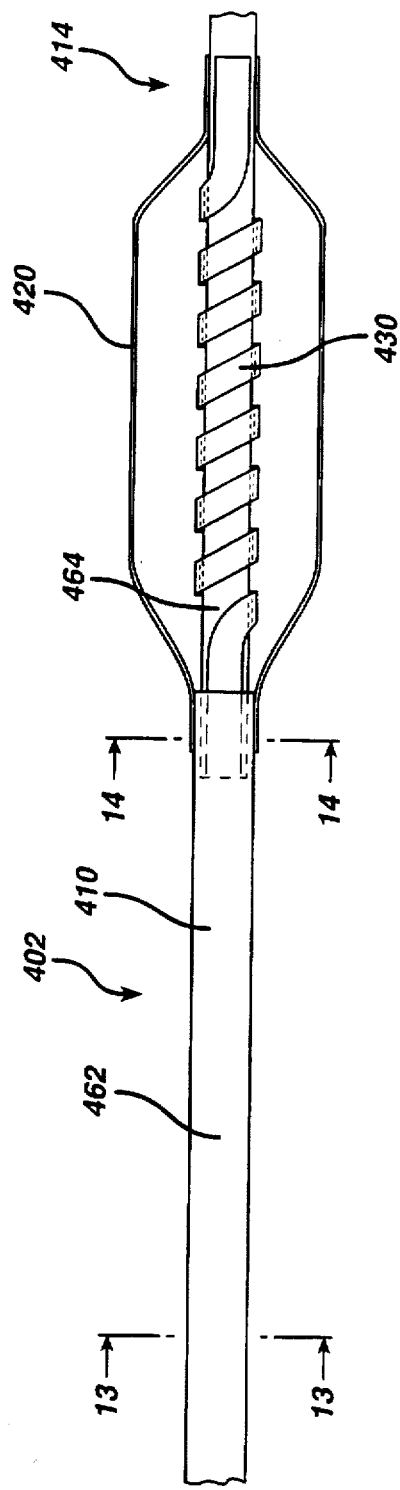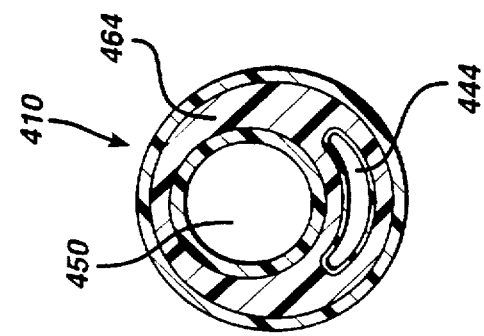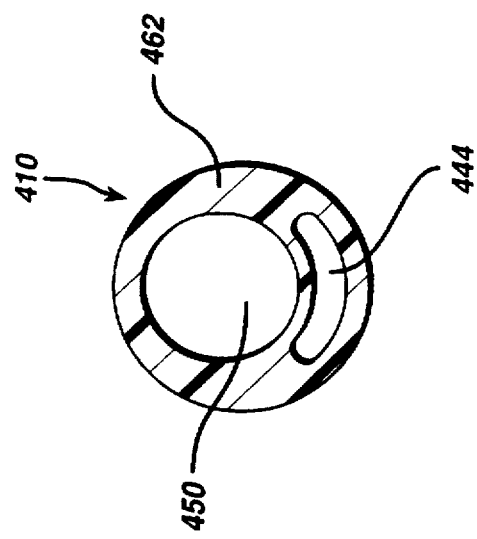
FIG. 12
FIG. 13
FIG. 14

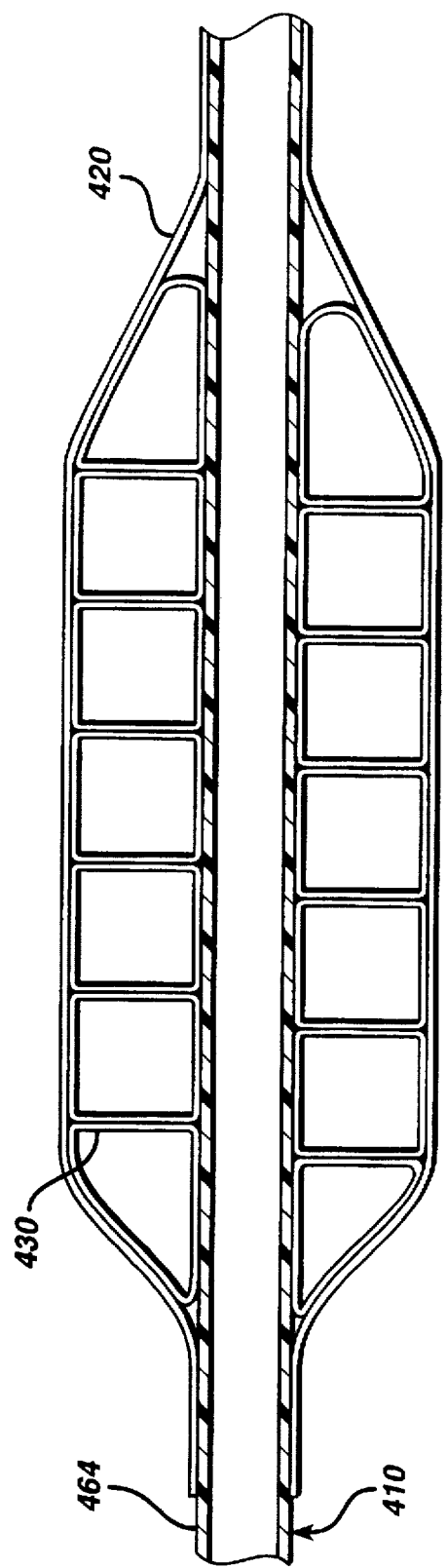

5,797,948

1

CENTERING BALLOON CATHETER

This is a continuation in part of U.S. application Ser. No. 08/725,364 filed on Oct. 3, 1996.

FIELD OF THE INVENTION

The present invention relates to medical catheters, such as balloon catheters. The present invention has even further relation to such catheters which are designed to center a lumen of the catheter within a body vessel.

BACKGROUND OF THE INVENTION

Restenosis after arterial intervention in general, and after percutaneous transluminal coronary angioplasty ("PTCA") in particular, is a primary concern of physicians practicing PTCA today. Conventional PTCA is performed using a standard balloon catheter such as the type described in U.S. Pat. No. 5,304,197 issued to Pinchuk et al. on Apr. 19, 1994, which is hereby incorporated herein by reference. Balloon catheters are typically used with a guidewire which is inserted into the patient's artery until its distal end is advanced past the diseased or stenotic area of the vessel, where there is a buildup of material. Balloon catheters typically have a guidewire lumen so that the proximal end of the guidewire can be inserted into the distal end of the balloon catheter. Thereafter, the balloon catheter is advanced over the guidewire until the balloon is adjacent the buildup of material. The balloon is then inflated to compress the buildup. Finally, the balloon is deflated and the catheter is pulled back up the guidewire and removed from the patient's artery. Restenosis of the artery often occurs after this procedure. That is the same area of the vessel collapses or becomes clogged again.

Recent technology has discovered that treating the diseased area of the vessel with radiation, after balloon angioplasty, helps prevent restenosis. Such technology is described in U.S. Pat. No. 5,199,939 issued to Dake et al. on Apr. 6, 1993, which is hereby incorporated herein by reference. Current technology contemplates the delivery of unspecified doses of radiation via wires having radioactive distal tips. A catheter would be inserted into the vasculature and advanced to the site of the previous angioplasty. The radioactive source wire would then be advanced through a lumen in the catheter so that its radioactive tip is adjacent the diseased site and can deliver the requisite amount of radiation. Thereafter the catheter and wire are removed. Such a device is described in PCT Application PCT/US94/04857 having an international publication number WO 94/25106 and publication date of Nov. 10, 1994.

Because the intensity of the radiation delivered to the vessel wall varies in inverse proportion to the square of the distance between the radioactive source and the vessel wall, it is desirable to center the radioactive wire within the vessel. This is also true when exposing a vessel to a light source. This prevents areas of the vessel from being overexposed or underexposed to the radiation. One such way to center the radioactive wire would be to deliver the wire to the site via a central lumen of a spiral balloon catheter. An example of a spiral catheter is given in U.S. Pat. No 4,762,130 issued to Fogarty et al. on Aug. 9, 1988, which is hereby incorporated herein by reference.

When using a spiral balloon in a vessel, the balloon is wrapped in a spiral fashion around a centering lumen. Likewise, a balloon could be molded in a spiral shape around the centering lumen. When inflated, the outer surface, or major diameter of the balloon pushes against the vessel wall, while the inner surface, or minor diameter, of the balloon pushes the centering lumen towards the center of the vessel. This centering effect increases as the pitch of the turns of the spiral balloon decreases.

Another example of a centering catheter is disclosed in European Patent Application number 94109858.4 filed on Jun. 24, 1994 by Schneider (Europe) AG. This type of catheter is often referred to as a segmented balloon catheter. It centers a centering lumen using the same principle as the spiral balloon catheter. However, instead of having a spiral it has a series of peaks and valleys created by segmenting an ordinary balloon catheter.

When delivering a radiation or light source to a vessel, an angioplasty operation is typically performed first. That is a physician first inserts an angioplasty balloon to the diseased portion of the artery and inflates the balloon to compress any deposits that have built up there. Thereafter, the physician removes the angioplasty balloon catheter and inserts the centering catheter. Centering catheters, such as spiral and segmented catheters, are impractical for performing angioplasty because they have areas which do not contact the vessel wall, thereby leaving un-compressed deposits within the vessel. There has been a desire to have a single catheter which can perform an angioplasty and, thereafter, can deliver and center a radioactive source wire. This would relieve the physician from having to remove and replace catheters during the procedure. The present invention is intended to provide such a catheter.

SUMMARY OF THE INVENTION

In accordance with the present invention, there is provided a catheter for insertion into a vessel of a patient. The catheter has distal and proximal ends and is made from an elongated flexible shaft also having distal and proximal ends. The shaft has a central lumen extending therethrough which is substantially centered within the shaft. The shaft also having distal and proximal ends and further includes an inflation lumen. The catheter includes an inflatable, preferably non-compliant, outer balloon disposed at its distal end and an inflatable, preferably compliant, inner balloon disposed within the outer balloon. The inner balloon is in fluid communication with the inflation lumen for inflation and deflation thereof. The central lumen extends through the inner balloon. The inner balloon is a centering balloon, whereby when it is at least partially inflated the distal end of said central lumen is substantially centered within the vessel.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

FIG. 9 is a view similar to that of FIG. 1 but showing an alternative embodiment of the present invention.

FIG. 10 is a cross-sectional view of the catheter shown in FIG. 9 taken along line 10—10.

FIG. 11 is a cross-sectional view of the catheter shown in FIG. 9 taken along line 11—11.

FIG. 12 is a view similar to that of FIG. 1 but showing an alternative embodiment of the present invention.

FIG. 13 is a cross-sectional view of the catheter shown in FIG. 12 taken along line 13—13.

FIG. 14 is a cross-sectional view of the catheter shown in FIG. 12 taken along line 14—14.

FIG. 15 is view similar to that of FIG. 2 but showing a cross-sectional view of the distal end of a balloon catheter of FIG. 12.

DETAILED DESCRIPTION OF THE INVENTION

Figure 1:
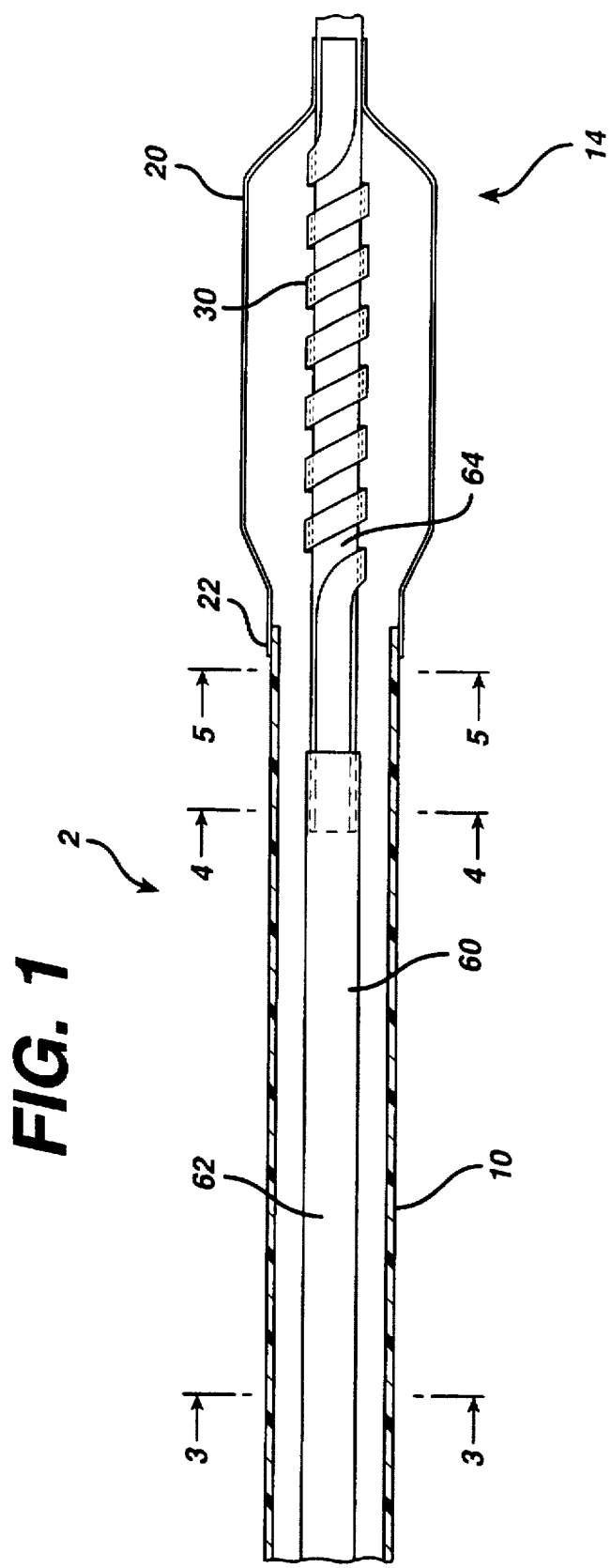
FIG. 1 is a simplified cross-sectional view of a distal end of a catheter made in accordance with the present invention wherein the outer balloon is inflated and the inner balloon is deflated.
Figure 2:
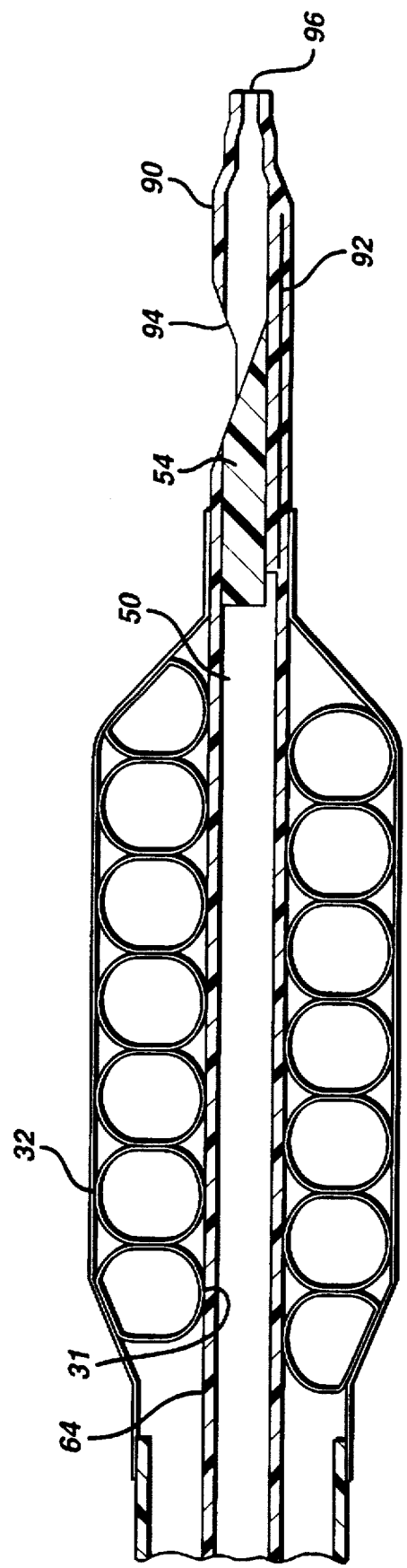
FIG. 2 is a cross-sectional view of the distal end of a balloon catheter made in accordance with the present invention, similar to that of FIG. 1, but showing a cross-section of the inner balloon as well, and also showing the inner balloon inflated.

Referring to the drawings wherein like numerals indicate the same elements throughout the views, there is shown in FIG. 1a catheter 2 made in accordance with the present invention. Catheter 2 is designed to be inserted into a vessel of a patient. Catheter 2 has a proximal end 12 (not shown) and a distal end 14. Catheter 2 has an elongated flexible outer shaft 10 and an elongated flexible inner shaft 60. Inner shaft 60 extends through the outer shaft 10 and has a central lumen 50 extending therethrough. Shaft 60 has a proximal portion 62 and a distal portion or distal end 64. Distal portion 64 is designed to be centered within the vessel of the patient. Distal end 14 of catheter 2 includes an inflatable outer balloon 20 and an inflatable inner balloon 30, disposed within outer balloon 20. Distal end 64 of shaft 60 extends through inner balloon 30, and inner balloon 30 is capable of centering distal end 64 within a body vessel once it is inflated. FIGS. 1 and 2 show the inner balloon 30 as a spiral balloon catheter which surrounds inner shaft 60.

As seen in the figures, and as will be appreciated by those skilled in the art, the inner and outer balloon assembly is a separate piece which is attached to shaft 10. The balloon assembly includes distal portion 64 of shaft 60, which is inserted into proximal portion 62 of shaft 60, to form the entire inner shaft 60. Outer balloon 20 has annular proximal portion 22 which is fitted over shaft 10. Proximal portion 22 is sealed to shaft 10 by any suitable means known in the art, such as heat sealing or adhesive sealing, so that the seal can withstand ordinary angioplasty pressures. Outer balloon 20 is preferably a substantially non-compliant PTCA dilation balloon, and made from any suitable material known in the art, including nylon. Such PTCA balloons are disclosed in the hereinbefore incorporated U.S. Pat. No. 5,304,197.

Inner balloon 30 can be made from any number of substantially non-compliant materials known in the art such as nylon or any number of substantially compliant materials known in the art such as silicon, latex and polyurethane. As mentioned above, inner balloon 30 is preferably a spiral balloon. It can be molded into a spiral shape by blow molding, injection molding etc. Alternatively, the balloon can be manufactured as a non-spiral balloon and then wrapped around central shaft 60 so as to have a spiral or helical configuration. Inner balloon 30 is designed to center distal end 64 of shaft 60 within the vessel of a patient. The spiral balloon has an inner surface 31 which is oriented so as to make contact with distal portion 64, and outer surface 32 which is oriented so as to make contact with outer balloon 20 and, consequently, the wall of the vessel. When balloon 30 is inflated, surface 32 pushes against the wall of the vessel, while surface 31 pushes against distal portion 64. This action causes distal end 64 of shaft 60, and hence central lumen 50 extending therethrough, to be centered within the vessel.

Figure 3:
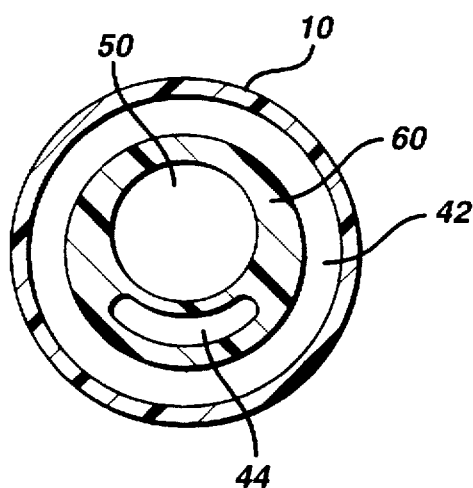
FIG. 3 is a cross-sectional view of the catheter shown in FIG. 1, taken along line 3—3.
Figure 4:
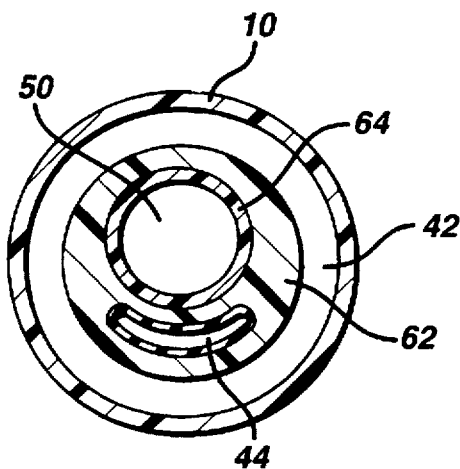
FIG. 4 is a cross-sectional view of the catheter shown in FIG. 1, taken along line 4—4.
Figure 5:
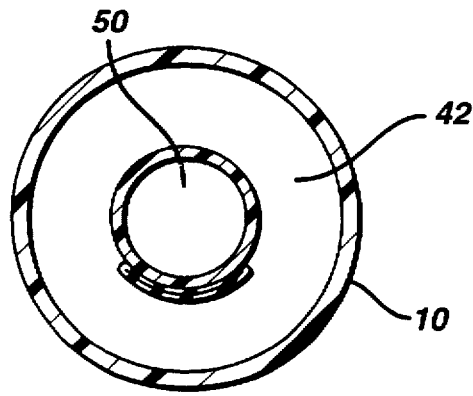
FIG. 5 is a cross-sectional view of the catheter shown in FIG. 1, taken along line 5—5.

Catheter 2 includes inflation lumens for inflating the two balloons. Preferably, the catheter has first and second inflation lumens extending through at least one of the inner and outer shafts. The outer balloon is in fluid communication with the first inflation lumen for inflation and deflation thereof. The inner balloon is in fluid communication with the second inflation lumen for inflation and deflation thereof. A preferred embodiment of the inflation lumens can be described by referring to FIGS. 3 and 4. As can be seen first inflation lumen 42 is an annular lumen and is in fluid communication with outer balloon 20. Second inflation lumen 44 extends through central shaft 60, which is a dual lumen shaft. FIGS. 3 and 4 also show central lumen 50 which, as described below, is for the insertion of a radioactive source wire. Lumens 44 and 50 could be co-axial or concentric. FIGS. 3 and 4 show that the central lumen is not necessarily centered within shaft 60 at the proximal portion 62. However, at the distal end 64 of shaft 60 the central lumen 50 is centered within shaft 60. The inflation lumen 44 is replaced by the inner balloon 30 itself and therefore is no longer needed within shaft 60. Therefore the arrangement of shaft 60 changes. This can best be described by referring to FIG. 5. FIG. 5 shows a cross-section of shaft 60 at its distal end, taken along FIG. 5—5.

Catheter 2 preferably includes a guidewire lumen for receiving a guidewire to help deliver the catheter. The guidewire lumen could simply be a short lumen which is distal of balloons 20 and 30. Such an arrangement is well known in the art and is often referred to as a distal channel guide wire lumen. This feature can best be described by referring to FIG. 2. FIG. 2 shows the catheter as having a guidewire lumen 90 on the distal end of catheter 2. Guidewire lumen 90 could include a support member 92. Support member 92 is shown as being a small wire located at the bottom and of the lumen. Lumen 90 has an entrance port 94 and an exit port 96 to accommodate a guidewire being placed therethrough. However, if the central lumen 50 is not required to be sealed at its distal end, it could act as the guidewire lumen as well. That is a steerable guidewire would be inserted through the lumen 50 in order to guide the balloon to the diseases site. Thereafter, the steerable guidewire is removed and the radioactive guidewire is inserted.

Central lumen 50 is designed to be centered within the vessel of a patient. The lumen is designed to receive a radioactive source wire. To prevent direct contact between blood and the radioactive source, the radioactive source wire should have a protective sleeve, or lumen 50 should be closed at its distal end, unlike an ordinary guidewire lumen. FIG. 2 shows the catheter 2 having a plug 54 which is distal to the spiral balloon 30. Plug 42 can be made from any suitable material such a polymer which is fuses within the lumen 50, or it could comprise an adhesive. An example of a catheter having a closed, radioactive source wire lumen is disclosed in U.S. Pat. No. 5,503,613 issued to Weinberger on Apr. 2, 1996, which is hereby incorporated herein by reference. Central lumen 50 must be large enough to allow for easy maneuvering of a radioactive source wire. Suitable diameters range from 0.010 inch to 0.050 inches. Shaft 60 should be thick enough and strong enough to prevent the radioactive source wire from puncturing through the shaft.

In addition to the present invention providing the advantage of an angioplasty and centering balloon in the same catheter, it also has other advantages. One such advantage is that it allows the manufacture of large centering balloons for use in the peripherals or the like. Currently, it is difficult to manufacture a large spiral non-compliant balloon catheter using blow molding techniques due to the large ration between the peaks and valleys, i.e. major diameter and minor diameter, of the balloon. However, it is practical to manufacture large diameter compliant balloon catheters by wrapping a compliant balloon around a shaft, or tacking/restraining a compliant balloon to a shaft to form a segmented balloon. However, compliant balloons run the risk of over expanding and damaging the vessel wall. With the present invention, the outer balloon can be made non-compliant to help prevent a compliant inner balloon from being over expanded during the centering procedure.

The present invention also allows PTCA procedures and radiation therapy to be performed by the same catheter. The present invention can be used by inserting the catheter into the vasculature of a patient and directing it to a constricted area through the use of a steerable PTCA guidewire. Thereafter, outer balloon 20 is inflated, thereby compressing the deposits on the artery. Balloon 20 is then deflated or vented and balloon 30 is inflated, so as to center lumen 50 within the vessel. Thereafter, a radioactive source wire can be advanced through lumen 50 so that it is adjacent the diseased area of the vessel. After the vessel receives the requisite amount of radiation, the radioactive source wire is removed. The inner balloon 30 is then deflated and the catheter is removed from the vessel.

Figure 6:
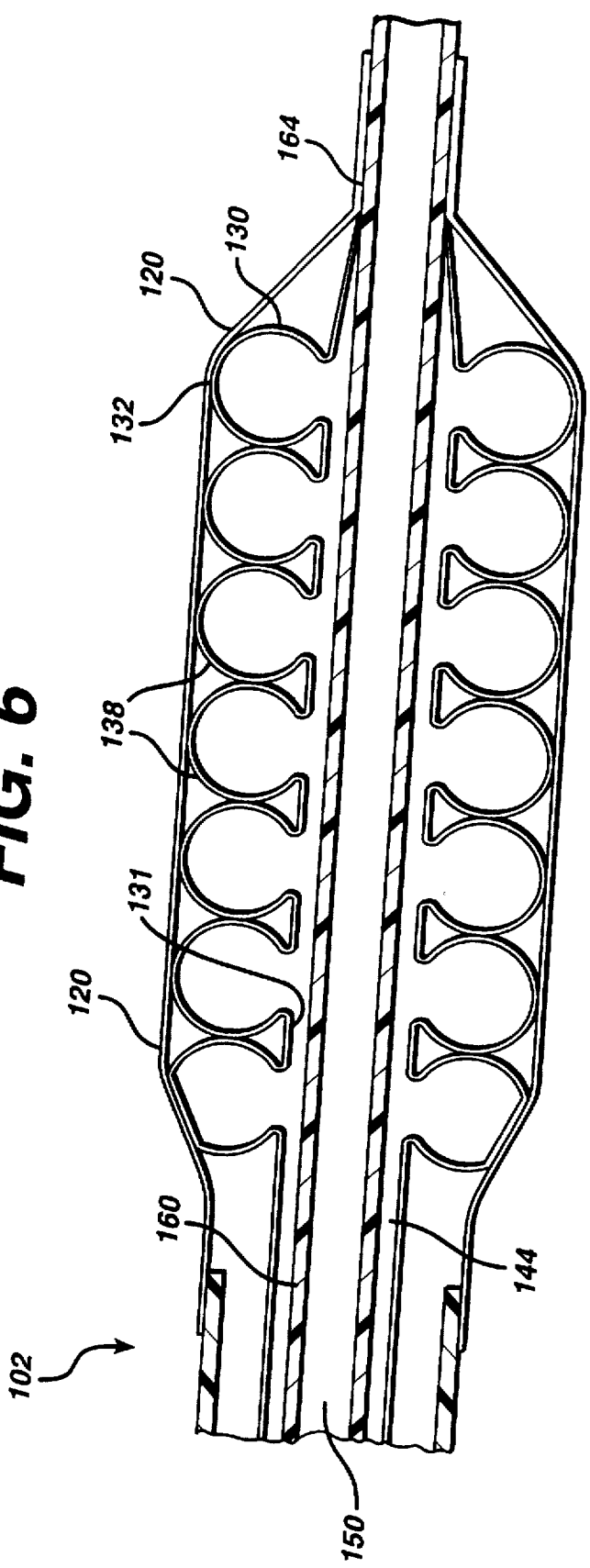
FIG. 6 is a view similar to that of FIG. 2 but showing an alternative embodiment of the present invention.

FIGS. 1 and 2 show the inner balloon 30 as a spiral balloon. However, the inner balloon of the present invention can be a segmented balloon. FIG. 6 shows a catheter 102, which is an alternative embodiment of the present invention. Catheter 102 is similar to catheter 2 except that inner centering balloon 130 is a segmented balloon. Balloon 130 is molded, from any suitable materials such as nylon, such that it has a series of semi-circular cross-sectional segments 138 which surround or are concentric with shaft 160. Alternatively, balloon 130 could be made from a compliant material and tacked/restrained to 164. Inflation lumen 144 extends along the length of balloon 130 such that each segment 138 is in fluid communication with the others. Balloon 130 centers the distal end 164 of shaft 160 much in the same way a spiral balloon would. Balloon 130 has an inner surface 131 which makes contact with the fluid in the inflation lumen 144, and outer surface 132 which is oriented so as to make contact with outer balloon 120 and, consequently, the wall of the vessel. When balloon 130 is inflated, surface 132 pushes against the wall of the vessel, while surface 131 pushes against the fluid in lumen 144 which in turn pushes against distal portion 164. This action causes distal end 164 of shaft 160, and hence central lumen 150 extending therethrough, to be centered within the vessel.

Figure 7:
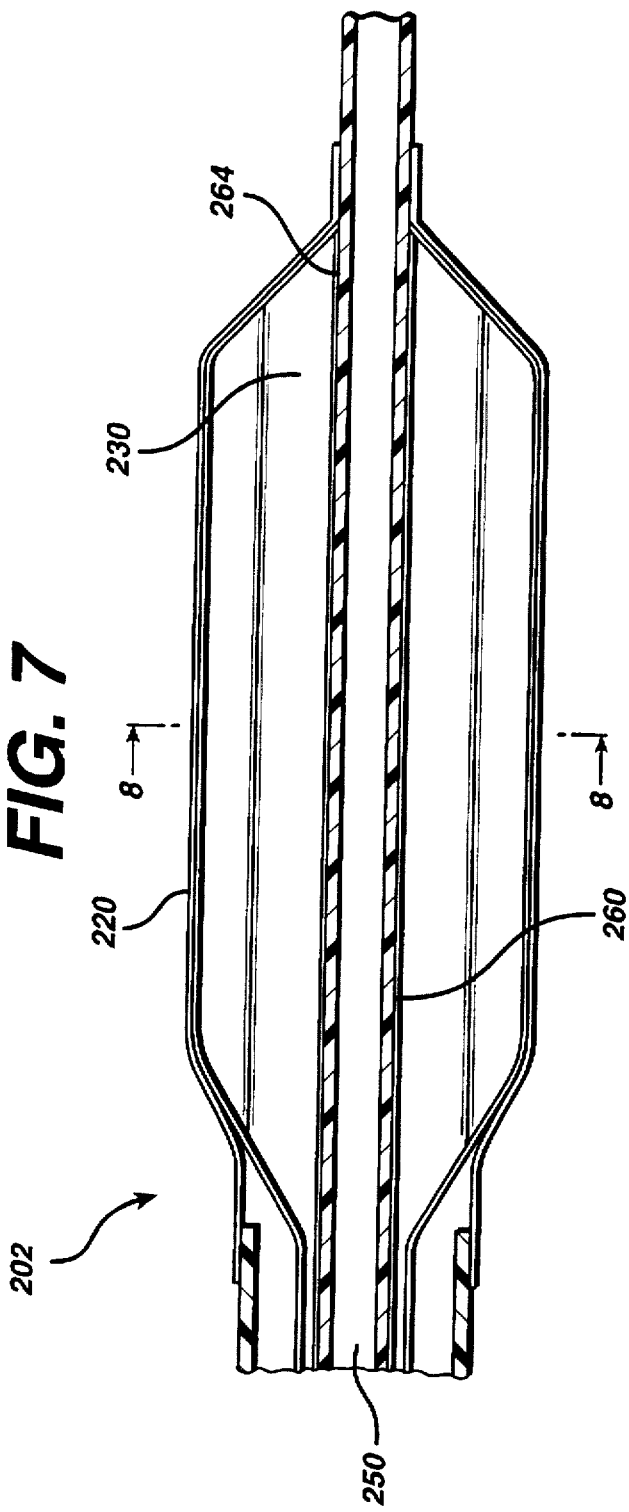
FIG. 7 is a view similar to that of FIG. 2 but showing yet another alternative embodiment of the present invention.
Figure 8:
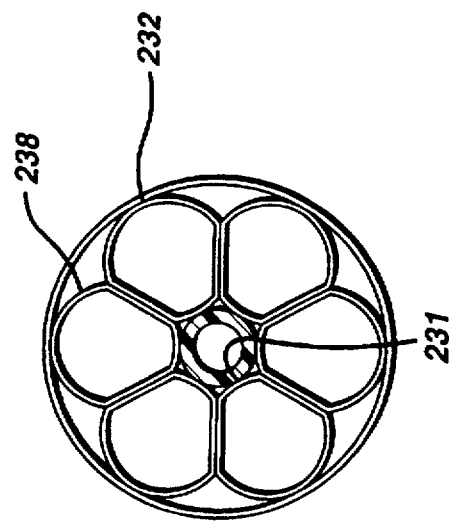
FIG. 8 is a cross-sectional view of the catheter shown in FIG. 7 taken along lines 8—8 and showing the centering catheter in its inflated state.

Another alternative embodiment of the catheter of the present invention is shown in FIG. 7. FIG. 7 shows catheter 202, which is an alternative embodiment of the present invention. Catheter 202 is similar to catheter 2 except that inner centering balloon 230 is a multiple axial chamber balloon. Balloon 230 is molded, from any suitable materials such as nylon, latex, etc. such that it has a series of axial segments 238 which extend substantially parallel to shaft. Balloon 230 centers the distal end 264 of shaft 260 much in the same way a spiral balloon would. Segments 238 have an inner surfaces 231 which make contact with distal portion 264, and outer surfaces 232 which are oriented so as to make contact with outer balloon 220 and, consequently, the wall of the vessel. When balloon 230 is inflated, surfaces 232 push against the wall of the vessel, while surfaces 231 push against the distal portion 164. This action causes distal end 264 of shaft 260, and hence central lumen 250 extending therethrough, to be centered within the vessel.

Another alternative embodiment of the catheter of the present invention is shown in FIGS. 9–11. FIGS. 9–11 show a catheter 302 which is similar to catheter 2. For the embodiments described above, all of the catheters had an inner shaft which extended through most of the length of the outer shaft. However, the present invention could be made using a single multi-lumen flexible shaft proximal to balloons 320 and 330, and having the inner shaft extend distally therefrom. As seen from FIG. 10, flexible outer shaft 310 has a central lumen 350, a first inflation lumen 342, and a second inflation lumen 344, all extending therethrough. As seen from FIG. 11, inner shaft 360 extends from the distal end 318 of outer shaft 310, and into balloon 320. In this embodiment, the inner shaft need not extend through the outer shaft.

Yet another embodiment of the present invention is shown in FIGS. 12—15. For this embodiment, the catheter 402 has only a single inflation lumen, which communicates with the inner balloon. This reduces the size of the catheter shaft because one of the inflation lumens is eliminated. Catheter 402 has a proximal end 412 (not shown) and a distal end 414. Catheter 402 has an elongated flexible shaft 410. Shaft 410 has a central lumen 450 extending therethrough. Shaft 410 has a proximal portion 462 and a distal portion or distal end 464. Distal end 414 of catheter 402 includes an inflatable outer balloon 420 and an inflatable inner balloon 430, disposed within outer balloon 420. Distal portion 464 of shaft 410 extends the central lumen 450 through inner balloon 430. Inner balloon 430 is capable of centering the distal end of the central lumen 450 within a body vessel once it is at least partially inflated.

In this embodiment it is preferable that the inner balloon be substantially compliant and that the adjacent turns, or peaks and valleys of the balloon be close enough so that the inner balloon substantially fills into the space of the outer balloon 420, as shown in FIG. 15. This allows an angioplasty procedure to be more effectively performed by a spiral balloon because it substantially eliminates gaps in the balloon at the vessel wall. This will work for the segmented balloons discussed above as long as the segments are spaced close enough together. Preferably the outer balloon is less compliant than the inner balloon, or most preferably if the outer balloon is substantially non-compliant and the inner balloon is substantially compliant. In this arrangement, the outer balloon would keep the inner balloon from over expanding and possibly rupturing.

In practice, the physician would insert the balloon to the target site. The inner balloon would then be fully inflated, as shown in FIG. 15, so as to perform an angioplasty. Thereafter, the physician can then insert a radioactive source wire or the like through the central lumen. The source wire would be substantially centered within the vessel. This allows the physician to perform the angioplasty and the radiation treatment at the same time.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A catheter for insertion into a vessel of a patient, said catheter having distal and proximal ends, said catheter comprising:
   a. an elongated flexible shaft having distal and proximal ends, said shaft having a central lumen extending therethrough, said central lumen also having distal and proximal ends, said shaft further including an inflation lumen;
   b. an inflatable outer balloon disposed at said distal end of said catheter, an inflatable inner balloon disposed within said outer balloon, said inner balloon being in fluid communication with said inflation lumen for inflation and deflation thereof, said central lumen extending through said inner balloon and said inner balloon being a centering balloon which pushes against both said vessel and said shaft when inflated whereby when said inner balloon is at least partially inflated said distal end of said central lumen is substantially centered within said vessel.

2. The catheter according to claim 1 wherein said outer balloon is less compliant than said inner balloon.

3. The catheter according to claim 1 wherein said central lumen is sealed at its distal end so as to substantially prevent the flow of fluid therethrough.

4. The catheter according to claim 1 further including a guidewire lumen.

5. The catheter according to claim 4 wherein said guidewire lumen comprises a tubular channel disposed distally of said inner and outer balloons, said channel adapted to receive said guidewire.

6. A catheter for insertion into a vessel of a patient, said catheter having distal and proximal ends, said catheter comprising:
   a. an elongated flexible shaft having distal and proximal ends, said shaft having a central lumen extending therethrough, said central lumen also having distal and proximal ends, said shaft further including an inflation lumen; and
   b. an inflatable substantially non-compliant outer balloon disposed at said distal end of said catheter, an inflatable substantially compliant inner balloon disposed within said outer balloon, said inner balloon being in fluid communication with said inflation lumen for inflation and deflation thereof, said central lumen extending through said inner balloon and said inner balloon being a centering balloon which pushes against both said vessel and said shaft when inflated whereby when said inner balloon is at least partially inflated said distal end of said central lumen is substantially centered within said vessel.

7. The catheter according to claim 6 wherein said central lumen is sealed at its distal end so as to substantially prevent the flow of fluid therethrough.

8. The catheter according to claim 6 further including a guidewire lumen.

9. The catheter according to claim 8 wherein said guidewire lumen comprises a tubular channel disposed distally of said inner and outer balloons, said channel adapted to receive said guidewire.

10. A catheter for insertion into a vessel of a patient, said catheter having distal and proximal ends, said catheter comprising:
    a. an elongated flexible shaft having distal and proximal ends, said shaft having a central lumen extending therethrough, said central lumen also having distal and proximal ends and being sealed at its distal end so as to substantially prevent the flow of fluid therethrough, said shaft further including an inflation lumen;
    b. an inflatable substantially non-compliant outer balloon disposed at said distal end of said catheter, an inflatable substantially compliant inner balloon disposed within said outer balloon, said inner balloon being in fluid communication with said inflation lumen for inflation and deflation thereof, said central lumen extending through said inner balloon and said inner balloon being a centering balloon which pushes against both said vessel and said shaft when inflated whereby when said inner balloon is at least partially inflated said distal end of said central lumen is substantially centered within said vessel; and
    c. a guidewire lumen comprising a tubular channel disposed distally of said inner and outer balloons, said channel adapted to receive said guidewire.

11. A catheter for insertion into a vessel of a patient, said catheter having distal and proximal ends, said catheter comprising:
    a. an elongated flexible shaft having distal and proximal ends, said shaft having a central lumen extending therethrough, said central lumen also having distal and proximal ends, said shaft further including an inflation lumen;
    b. an inflatable outer balloon disposed at said distal end of said catheter, an inflatable inner balloon disposed within said outer balloon, said inner balloon being in fluid communication with said inflation lumen for inflation and deflation thereof, said central lumen extending through said inner balloon and said inner balloon being a centering balloon comprising spiral balloon surrounding a predetermined portion of said distal end of said central lumen whereby when said inner balloon is at least partially inflated said distal end of said central lumen is substantially centered within said vessel.

12. The catheter according to claim 11 wherein said inner balloon is substantially non-complaint and said outer balloon is substantially compliant.

13. The catheter according to claim 12 further including a guidewire lumen comprising a tubular channel disposed distally of said inner and outer balloons, said channel adapted to receive said guidewire.

14. A catheter for insertion into a vessel of a patient, said catheter having distal and proximal ends, said catheter comprising:
    a. an elongated flexible shaft having distal and proximal ends, said shaft having a central lumen extending therethrough, said central lumen also having distal and proximal ends, said shaft further including an inflation lumen;
    b. an inflatable outer balloon disposed at said distal end of said catheter, an inflatable inner balloon disposed within said outer balloon, said inner balloon being in fluid communication with said inflation lumen for inflation and deflation thereof, said central lumen extending through said inner balloon and said inner balloon being a centering balloon comprising a segmented balloon having a plurality of annular segments, said plurality of annular segments surrounding a predetermined portion of said distal end of said central lumen whereby when said inner balloon is at least partially inflated said distal end of said central lumen is substantially centered within said vessel.

15. The catheter according to claim 14 wherein said inner balloon is substantially non-compliant and said outer balloon is substantially compliant.

16. The catheter according to claim 15 further including a guidewire lumen comprising a tubular channel disposed distally of said inner and outer balloons, said channel adapted to receive said guidewire.

17. A catheter for insertion into a vessel of a patient, said catheter having distal and proximal ends, said catheter comprising:

a. an elongated flexible shaft having distal and proximal ends, said shaft having a central lumen extending therethrough, said central lumen also having distal and proximal ends, said shaft further including an inflation lumen;

b. an inflatable outer balloon disposed at said distal end of said catheter, an inflatable inner balloon disposed within said outer balloon, said inner balloon being in fluid communication with said inflation lumen for inflation and deflation thereof, said central lumen extending through said inner balloon and said inner balloon being a centering balloon comprising a plurality of longitudinal segments, wherein each segment is substantially parallel to said inner shaft, said plurality of segments substantially surrounding a predetermined portion of said distal end of said central lumen whereby when said inner balloon is at least partially inflated said distal end of said central lumen is substantially centered within said vessel.

18. The catheter according to claim 17 wherein said inner balloon is substantially non-compliant and said outer balloon is substantially compliant.

19. The catheter according to claim 18 further including a guidewire lumen comprising a tubular channel disposed distally of said inner and outer balloons, said channel adapted to receive said guidewire.

* * * * *